United States Patent [19]

Shih et al.

[11] Patent Number: 4,923,694

[45] Date of Patent: May 8, 1990

[54] HYDROLYSIS RESISTANT VINYL LACTAM AMINO ACRYLAMIDE POLYMERS

[75] Inventors: Jenn S. Shih, Paramus; Terry E. Smith, Morristown, both of N.J.

[73] Assignee: GAF Chemicals Corporation, Wayne, N.J.

[21] Appl. No.: 236,395

[22] Filed: Aug. 25, 1988

[51] Int. Cl.$^5$ ................................................ A61K 7/11
[52] U.S. Cl. ...................................... 424/70; 424/78; 424/DIG. 2; 424/71
[58] Field of Search ...................... 528/264; 429/78, 70, 429/71, DIG. 2

[56] References Cited

U.S. PATENT DOCUMENTS

| | | | |
|---|---|---|---|
| 2,344,934 | 3/1944 | West | 564/47 X |
| 2,980,657 | 4/1961 | Melamed | 526/264 X |
| 3,914,403 | 10/1975 | Valan | 424/47 |
| 3,954,960 | 5/1976 | Valan | 424/70 X |
| 4,057,533 | 11/1977 | Hort et al. | 526/264 X |
| 4,521,404 | 6/1985 | Lorenz et al. | 424/70 X |

Primary Examiner—Ellis P. Robinson
Assistant Examiner—Susan S. Rucker
Attorney, Agent, or Firm—Marilyn J. Maue; Joshua J. Ward

[57] ABSTRACT

The invention relates to a hydrolysis resistant, high molecular weight polymer represented by the formula

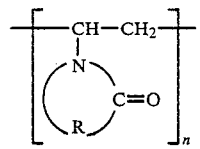

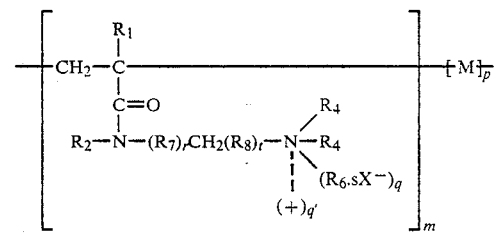

wherein R is alkylene having from 3 to 8 carbon atoms which is optionally substituted with lower alkyl; $R_1$ and $R_2$ are each hydrogen or methyl; wherein $R_7$ and $R_8$ are each alkylene having from 1 to 18 carbon atoms and are optionally substituted with alkyl; the sum of r and t is one or two; $R_4$ and $R_5$ are each independently lower alkyl; $R_6$ is alkyl, aralkyl or alkaryl having from 1 to 8 carbon atoms or N-alkylene lactam having from 3 to 8 carbon atoms; $X^-$ is an anion derived from the group of halogen, $SO_3$, $SO_4$, $HSO_4$ and $R_6SO_4$; M is a copolymerizable vinyl monomer; n has a value of from 10 to 99 mole %; m has a value of from 1 to 90 mole %; p has a value of from 0 to 20 mole % and the sum of m+n+p is 100; q and q' have the same value which is 0 or 1; s is the reciprocal of the number of negative charges in X; and the total amount of monomer represented by subscript m can be from 1% to 100% quaternized. The invention also relates to a process for the preparation of the polymer containing low residual monomer and to uses of the polymer.

3 Claims, No Drawings

HYDROLYSIS RESISTANT VINYL LACTAM AMINO ACRYLAMIDE POLYMERS

In one aspect this invention relates to a novel hydrolysis resistant high molecular weight polymer. In another aspect the invention relates to the preparation of said polymer and in still another aspect to methods of using said polymer in cosmetic formulations, such as hair sprays, hair conditioners, hair setting lotions, skin moisturizers, suntan lotions, etc.

BACKGROUND OF THE INVENTION

Several synthetic polymers containing vinyl lactams are presently used in cosmetic and textile formulations to provide high penetration of other active components, to contribute body and holding power to hair sprays, setting lotions, etc. and to promote softening and moistening in skin and body conditioners. Most of these synthetic polymers are comprised of vinyl lactam and acrylate or methacrylate monomers as in U.S. Pat. Nos. 3,954,960 and 3,914,403. While these copolymers provide excellent hair adhesion and set hold under conditions of high humidity, they are subject to excessive hydrolysis when formulated into cosmetic formulations at a pH greater than 7 and/or maintained at a elevated temperature, for example temperatures in excess of 40° C. for considerable time. Hydrolysis causes the polymer to decompose forming an alcohol amine which can result in significant lowering of viscosity and concomitant reduction in beneficial properties.

While the polymer of U.S. Pat. No. 4,057,533 overcomes some of the above disadvantages, such polymers containing the aminomethyl acrylamide moiety of this patent are known to be unstable and to decompose to methylol amide and an ammonium salt upon heating (see U.S. Pat. No. 2,344,934) or in the presence water (Journal of the Society of Dyers and Colourists, Volume 63, page 260, 1947 by F. V. Davis and SURFACE ACTIVITY, VanNostrand Press, 2nd Edition, 1961, page 241 by J. L. Moilliet, B. Collie and W. Black).

Accordingly, it is an object of this invention to overcome the above deficiencies without sacrifice to the above enumerated advantages. Another object of the invention is to provide a novel polymer suitable for use in cosmetic formulations and textile treating solutions.

Another object is to provide a commercially feasible and economical process for the preparation of the present polymers.

Still another object is to provide specific uses for the polymer of the present invention.

These and other objects will become apparent from the following description and disclosure.

THE INVENTION

According to this invention there is provided a hydrolysis resistant high molecular weight polymer having a structure defined by the formula

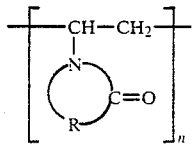

-continued

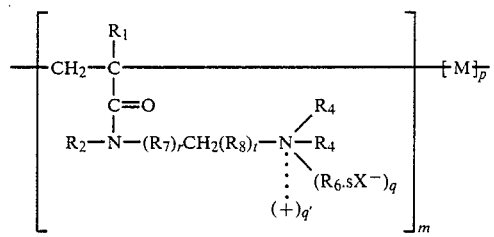

wherein R is alkylene having from 3 to 8 carbon atoms which is optionally substituted with lower alkyl; $R_1$ and $R_2$ are each hydrogen or methyl; $R_7$ and $R_8$ are each alkylene having from 1 to 18 carbon atoms and are optionally substituted with alkyl; the sum of r and t is one or two; $R_4$ and $R_5$ are each independently lower alkyl; $R_6$ is alkyl, aralkyl or alkaryl having from 1 to 8 carbon atoms or N-alkylene lactam having from 3 to 8 carbon atoms; $X^-$ is an anion selected from the group of chloride, bromide, iodide, $SO_3$, $SO_4$, $HSO_4$ and $R_6SO_4$; M is a copolymerizable vinyl monomer; n has a value of from 1 to 99 mole %; m has a value of from 1 to 90 mole %; p has a value of from 0 to 20 mole % and the sum of $m+n+p$ is 100; q and q' have the same value which is 0 or 1; s is the reciprocal of the number of negative charges in $X^-$; and the total amount of monomer represented by subscript m can be from 1 to 100% quaternized.

Of these polymeric products, those wherein R is alkylene having from 3 to 5 ring carbon atoms and wherein p has a value of zero and the monomer designated by subscript m is at least 20% quaternized are preferred. Most preferred of this group are those wherein said monomer is at least 30% quaternized, from 50% to 100% quaternized monomer being most desirable.

The present polymers possess many beneficial properties, among which is their ability to build viscosity, and to resist hydrolysis in alkaline solutions while simultaneously providing a hair and skin conditioning capability in cosmetic and personal care formulations. The polymers also have excellent hair and skin substantivity so that their conditioning effects endure for longer periods. They resist flaking, provide a softer, silkier texture to the hair and possess good hair and skin moisturizing. For the purpose of this invention, the term "conditioning" is intended to include the functions of moisturizing, softening, cleansing, penetrating, luster enhancing, hair combability, hair dye leveling, dye retention and others.

The present polymers are prepared by reacting the vinyl lactam, a tertiary amino acrylamide or quaternized amino acrylamide, and optionally a dissimilar vinyl monomer, and recovering the product as the product of the process or treating all or a portion of the non-quaternized polymer with an organic quaternizing agent to effect at least 20% quaternization of the amine.

Suitable lactam monomers employed to form the polymers of this invention include N-vinyl pyrrolidone, N-vinyl caprolactam, N-vinyl piperidone, 4-methyl-N-vinyl pyrrolidone, 3,5-dimethyl-N-vinyl caprolactam, N-vinyl-hexahydro-2-azepinone, N-vinyl-octahydro-2-azocinone, N-vinyl octahydro-2-azoninone, N-vinyl decahydro-2-azecinone, etc. and mixtures thereof wherein N-vinyl pyrrolidone comprises the major amount of the lactam portion. Of these, N-vinyl pyrrolidone, N-vinyl caprolactam and the ring substituted alkyl derivatives of the N-vinyl caprolactom and N-vinyl pyrrolidone monomers are preferred, N-vinyl-2-pyrrolidone being most preferred.

Tertiary amine acrylamide comonomers useful in preparing the polymers of the present invention include the tertiary amino acrylamides and methacrylamides of the general formula

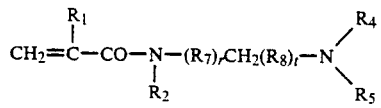

wherein $R_1$, $R_2$, $R_4$, $R_5$, $R_7$, $R_8$, r and t are as defined above. Suitable comonomers include the above non-quaternized monomers and corresponding monomers quaternized with suitable organic quaternizing agents such as dialkyl sulfates, for example, methyl ethyl sulfate, diethyl sulfate, dimethyl sulfate etc.; alkyl sulfonic acids, e.g., methyl sulfonic acid, ethyl sulfonic acid, etc.; benzyl halides, such as benzyl chloride, benzyl bromide, and benzyl iodide; alkyl halides, e.g. methyl chloride; N-halo lower alkyl lactams, e.g. N-chloromethyl pyrrolidone, N-bromoethyl-caprolactam, etc.; heterocyclic sulfonates, e.g. 1,2-oxathietane-2,2-di-one, N-[3-(dimethylamino)-1,1-dimethylpropyl]acrylamide, N-[4-(dimethylamino)-1,1-dimethylbutyl]metacrylamide, N-[3-(dimethylamino)-3-3-diethylpropyl]acrylamide, N-[4-(dimethylamino)-4,4-diethylbutyl]methacrylamide, 1,2-oxathiolane-2,2-di-one, 1,2-oxathiane-2,2-di-one; a lactone e.g., β-propiolactone, α-butyrolactone etc. In general, any organic quaternizing agent can be employed in the production of the quaternary N-vinyl pyrrolidone copolymers of the present invention. The quaternized amine acrylamide comonomers are those represented by the general formula

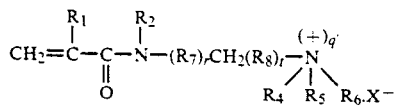

wherein $R_1$, $R_2$, $R_4$, $R_5$, $R_6$, $R_7$, $R_8$, r, t and q' are as defined above.

Examples of amino acrylamides which are employed as comonomers include

N-[12-(dimethylamino)dodecyl]methacrylamide;
N-[18-(dimethylamino)octadecyl]methacrylamide;
N-[8-(dimethylamino)octyl]methacrylamide;
N-[7-(dimethylamino)heptyl]acrylamide;
N-[14-(dimethylamino)tetradecyl]acrylamide;
N-[3-(dimethylamino)propyl]methacrylamide;
N-[3-(diethylamino)propyl]acrylamide;
N-[4-(dipropylamino)butyl]methacrylamide;
N-[3-(methyl butyl amino)propyl]acrylamide;
N-{2-[3-(dimethylamino)propyl]ethyl}acrylamide;
N-{4-[4-(diethylamino)butyl]butyl}acrylamide, etc.

and their corresponding quaternized salts and mixtures of these comonomers. Of the above group, the N-[3-(dimethylamino)alkyl]methacrylamides and acrylamides and their quaternized halide, sulfate and sulfonate salts are preferred. Of these, N-[3-(dimethylamino)propyl]methacrylamide; (3-methacrylamidopropyl) trimethylammonium chloride; (3-acrylamido-3-methylbutyl) trimethylammonium bromide; (3-methacrylamido-3-ethylbutyl) trimethylammonium chloride; (4-acrylamido-3-methylbutyl) trimethylammonium chloride; (3-methacrylamidopropyl) ethyl dimethylammonium ethyl sulfate and the 1,2-oxathiolane-2,2-di-one salt and the N-haloalkyl pyrrolidone salt of N-[3-(dimethylamino)propyl]methacrylamide are most preferred.

The optional vinyl monomer represented by M in the above formula can comprise any vinyl monomer which is copolymerizable with N-vinyl pyrrolidone. Thus, for example, suitable vinyl monomers include acrylic and methacrylic acid and esters thereof, e.g., methyl acrylate, methyl methacrylate, etc.; vinyl aromatic monomers, e.g., styrene, α-methyl styrene, etc.; vinyl acetate; vinylidene chloride; acrylonitrile and alkyl substituted derivatives thereof; methacrylonitrile and substituted derivatives thereof; acrylamide and methacrylamide and N-substituted derivatives thereof; vinyl chloride, crotonic acid and esters thereof; tertiary amino acrylates and tertiary amino methacrylates e.g., dimethylamino ethyl acrylate or methacrylate, dimethylamino propyl acrylate or methacrylate, diethylaminobutyl acrylate or methacrylate etc.

The preferred novel quaternized polymers of the present invention can be characterized as having a repeating structural units derived from A. 50–99 mole % of the vinyl lactam;
B. 1–50 mole % of a quaternized and/or non-quaternized lower alkylamino alkyl acrylamide or methacrylamide of which at least 20% is preferably quaternized and
C. 0–10 mole % of a vinyl monomer copolymerizable with vinyl pyrrolidone.

The polymer composition may also contain some small amount of residual monomer usually less than 7%, more desirably less than 2% of polymer solids. For incorporation into hair treating products, it is desired to restrict the quaternized portion of the polymeric product to not more than 50% since excessive quaternized moiety hinders ease of rinsability from the hair and renders the polymer less compatible with anionics, such as sodium or ammonium lauryl sulfate, lauryl ether sulfates, triethanol amines and others, often found in hair treatment compositions.

The polymers of the present invention are conveniently prepared by subjecting a solution of the vinyl lactam, preferably vinyl pyrrolidone, and the amino acrylamide or amino methacrylamide comonomers, in a quaternized or non-quaternized form, in the presence or absence of a dissimilar copolymerizable vinyl monomer, to conditions conductive to polymerization through double bonds. Thus, for example, the reaction can be suitably initiated by the action of free radicals, polymerization proceeding exothermically once initiated. Suitable free radical initiators conveniently employed and suitably utilized in accordance with the production of the copolymers of the present invention include organic and inorganic peroxide and perester compounds e.g., hydrogen peroxide, lauryl peroxide, decanoyl peroxide, di-tert-butyl peroxide, tert-butyl peroxypivalate, etc., aliphatic azo compounds, e.g., azobisisobutyronitrile, as well as other free radical initiators well known in the polymerization art.

The polymerization reaction of the present invention takes place in solution. Accordingly, any solvent which does not significantly interfere with polymerization of the monomers by chain transfer can be suitably employed. Typical solvents which can be employed especially for hair spray, hair conditioners and like applications, are the lower alcohols or water. However other solvents such as acetone, 2-butanone, etc. are also suitably employed in the polymerization.

The polymerization reaction is effected at a temperature between about 40° C. and about 130° C. under from about 14 to about 50 psia. for a period of from about 1 to about 20 hours. To avoid run away conditions and to obtain a copolymer of a desirable high molecular weight it is preferred to carry out the polymerization at the lower end of the temperature range, e.g. between about 50° C. and about 80° C. The polymerization reaction is preferably carried out in the absence of free oxygen, conveniently under a blanket of an inert gas, such as, nitrogen, argon or the like, and at atmospheric pressure.

As indicated above the present polymers can be quaternized or non-quaternized. For example between about 20% and 100%, most preferably between about 50% and 100%, of the tertiary amino acrylamide comonomer can be in the quaternized state. The quaternized moiety may be formed either before or after polymerization with lactam using between about 1 and about 90 wt. % of the organic quaternizing agent based on the tertiary amino amide employed. To obtain a prequaternized monomer the tertiary amino acrylamide is reacted with the quaternizing agent at a temperature of between about 20° C. and about 120° C. under atmospheric pressure until the desired amount of the salt product is obtained. Quaternization after the formation of the polymeric product is effected under similar temperature and pressure conditions.

Suitable quaternizing agents include di lower alkyl sulfate, $C_1$ to $C_{11}$ alkyl halide, dimethyl sulfonate, etc. Examples of initiators employed for the polymerization are azobisisobutyronitrile, lauroyl peroxide, hydrogen peroxide, benzoyl peroxide, t-butylperbenzoate, t-butylperoxypivalate and other peroxy type initiators.

As indicated previously, the novel polymers of the present invention are conveniently and economically obtained via the above-described polymerization techniques as high molecular weight, film-forming materials. In this regard, the polymers produced in accordance with the present invention are generally those having a Fikentscher K value within the range of 19 to 150 and more desirably within the range of 30 to 120 which corresponds approximately to a weight average molecular weight within the range of 15,000 to 5,000,000 more desirably, within the range of 60,000 to 3,000,000. Such copolymers in their unquaternized form or in the form of their quaternary salts are eminently useful as hair spray resins in that they form clear, flexible and easily removable films from both aqueous and alcoholic solutions and are resistant to hydrolysis at a pH as high as 10 or more and elevated temperatures.

The molecular weight of the copolymers of the present invention can be varied depending upon the particular choice of reactants, initiator, solvent and polymerization conditions, especially temperature, with the lower temperatures being conducive to the formation of higher molecular weight polymers.

In the preparation of the novel copolymers of the present invention, it is only necessary to mix the monomers in the ratios set forth above in order to provide a copolymer product produced through vinyl polymerization initiated by the action of free radicals. Generally, the copolymer is produced within a period of a few hours, e.g. less than about 10 hours.

The present polymeric products are also useful as viscosity builders for cosmetic creams and lotions as well as for hair treatment compositions to provide body and retentative moisturizing. When incorporated into standard formulations such as hair sprays, hair setting lotions, hair and skin conditioners, and other personal care products, the amount of polymeric product used can range between about 0.05 weight % and about 8 weight %, based on total formulation. Usually not more than 4% is required to achieve the above desirable affects. The present polymer or polymer mixture is conveniently added to the cosmetic formulations as an aqueous solution containing from about 10% to about 30% of polymer.

Having thus generally described the invention, reference is now had to the following examples which provide specific and preferred embodiments but which are not to be construed as limiting the scope of the invention as more broadly set forth above and in the appended claims.

EXAMPLES 1-8

Preparation of Vinyl Pyrrolidone/N-[3-(Dimethylamino)Propyl]methacrylamide Quaternized with Diethyl Sulfate Eight quaternized copolymers were prepared which incorporated varying amounts of monomers and quaternizing agent as shown in Table I. These reactions were carried out as follows.

A 1 liter four necked round bottom flask equipped with a mechanical stirrer, a dropping funnel, a condenser and a thermometer was charged with 600 g. of distilled water and N-vinyl pyrrolidone (VP) as noted in Table I. The solution was purged with nitrogen gas to provide an oxygen free atmosphere and heated to 62° C. for one half hour after which 2 g. of N-[3-(dimethylamino)propyl]methacrylamide (DMAPMAA) and 10 drops (0.2 g.) of t-butylperoxypivalate were added to the reaction flask. The solution was then heated to 67° C. The remaining portion of DMAPMAA, amounting to the total reported in Table I, was added into the flask drop by drop over a period of 2 hours. The solution was stirred for an additional 3 hours at 67° C. after which it was cooled to 43° C. and diethyl sulfate (DES) was charged over a period of 15-30 minutes. After a period of 3 hours at 43° C., the solution was cooled to room temperature and stirred overnight.

The respective product mixtures were recovered as a solution.

TABLE I

| EXAMPLE | VP (g) | DMAPMAA (g) | DES (g) | % of Quat. Amide |
|---------|--------|-------------|---------|------------------|
| 1 | 135 | 7.87 | 7.13 | 100 |
| 2 | 105 | 23.61 | 21.39 | 100 |
| 3 | 75 | 39.35 | 35.65 | 100 |
| 4 | 135 | 10.32 | 4.18 | 50 |
| 5 | 105 | 30.97 | 14.03 | 50 |
| 6 | 75 | 51.62 | 23.38 | 50 |
| 7 | 120 | 15.74 | 14.26 | 100 |
| 8 | 120 | 15.74 | 14.26 | 100 |

The corresponding non-quaternized polymers of Examples 1-8 are similarly prepared, except that the addition of quaternizing agent is omitted. These non-quaternized polymers show good compatability with anionic components used in personal care formulations and have improved skin and hair substantivity over polyvinyl pyrrolidone but are not as effective as their partially or totally quaternized counterparts.

EXAMPLES 9-18

Preparation of Vinyl Pyrrolidone/N-[3-(Dimethylamino)propyl]Methacrylamide Quaternized with Methyl Chloride Ten quaternized copolymers were prepared which incorporated varying amounts of monomers and quaternizing agent as shown in Table II. These reactions were carried out as follows.

To a 1 liter four necked round bottom flask which was equipped with a mechanical stirrer, a condenser, a thermometer and a dropping funnel, distilled water and VP were charged as noted in Table II. The solution was mixed, purged with nitrogen gas and heated up to 62° C. for one half hour. Unquaternized amide (DMAPMAA) and MAPTAC (50% aqueous solution of 100% of quaternized DMAPMAA obtained from Virginia Chemical Corp.) were well mixed in a beaker and 2 g. of the resulting solution and 10 drops (0.2 g.) t-butylperoxypivalate were charged into the reaction flask whereupon the resulting solution was heated to 67° C. The remaining portions of DMAPMAA and MAPTAC solution amounting to the total reported in Table II were then charged into the flask through a dropping funnel over a period of 2 hours. After the addition was complete, the solution was stirred for an additional 3 hours at 67° C. Finally, the solution was cooled to room temperature and stirred overnight.

The quaternized product was recovered as a liquid.

TABLE II

| Example No. | VP (g) | Water (g) | DMAPMAA (g) | MAPTAC. g. (a 50% aqueous soln.) | % of Quat. Amide |
|---|---|---|---|---|---|
| 9 | 120 | 600 | 30 | 0 | 0 |
| 10 | 120 | 570 | 0 | 60 | 100 |
| 11 | 135 | 585 | 0 | 30 | 100 |
| 12 | 105 | 555 | 0 | 90 | 100 |
| 13 | 75 | 525 | 0 | 150 | 100 |
| 14 | 135 | 592.5 | 7.5 | 15 | 50 |
| 15 | 105 | 577.5 | 22.5 | 45 | 50 |
| 16 | 75 | 562.5 | 37.5 | 75 | 50 |
| 17 | 135 | 585 | 0 | 30 | 100 |
| 18 | 75 | 525 | 0 | 150 | 100 |

The corresponding non-quaternized polymers of Examples 9-18 are similarly prepared, except that MAPTAC (3-methacrylamidopropyl) dimethyl ammonium chloride in the above MAPTAC solution is replaced with N-[3-(dimethylamino)propyl]methacrylamide (DMAPMAA).

The polymeric product mixtures obtained from the reactor in Examples 1-18 were analyzed and found to have the properties reported in following Table III.

TABLE III

| Polymer of Example | Appearance | Wt. % of (1) | Wt. % of (2) | Wt. % Residual VP (3) | Brookfield Viscosity (4) CP | Intrinsic Viscosity (5) dl/g |
|---|---|---|---|---|---|---|
| 1 | clear | 90/10 | 0/100 | 0.005 | 6500 | 1.33 |
| 2 | clear | 70/30 | 0/100 | 1.53 | 9000 | 1.78 |
| 3 | clear | 50/50 | 0/100 | 1.30 | 1250 | 1.26 |
| 4 | clear | 90/10 | 50/50 | 3.50 | 5500 | 1.56 |
| 5 | clear | 70/30 | 50/50 | 4.40 | 10800 | 1.92 |
| 6 | clear | 50/50 | 50/50 | 4.00 | 1740 | 1.28 |
| 7 | hazy | 80/20 | 0/100 | 1.53 | 4300 | 1.31 |
| 8 | hazy | 80/20 | 0/100 | 3.00 | 3700 | 1.39 |
| 9 | clear | 80/20 | 100/0 | 3.00 | 6920 | 1.81 |
| 10 | clear | 80/20 | 0/100 | 4.20 | 2480 | 1.52 |
| 11 | hazy | 90/10 | 0/100 | 3.30 | 4300 | 1.37 |
| 12 | clear | 70/30 | 0/100 | 3.40 | 2300 | 1.39 |
| 13 | hazy | 50/50 | 0/100 | 2.60 | 550 | 1.06 |
| 14 | clear | 90/10 | 50/50 | 2.60 | 10500 | 1.74 |
| 15 | clear | 70/30 | 50/50 | 4.50 | 29500 | 2.53 |
| 16 | clear | 50/50 | 50/50 | 4.90 | 1600 | 1.80 |
| 17 | hazy | 90/10 | 0/100 | 6.60 | 2900 | 1.48 |
| 18 | clear | 50/50 | 0/100 | 3.80 | 800 | 1.26 |

(1) vinyl pyrrolidone/total of DMAPMAA and its sulfate or chloride salt
(2) DMAPMAA/DMAPMAA sulfate or chloride salt
(3) measured by titration
(4) using LVF Brookfield viscometer, spindle #4, rpm 15, 30, 60 at 25° C.
(5) measured in 0.1 M LiNO₃ aqueous solution at 25° C.

The residual vinyl pyrrolidone content in the above products can be lowered by product purification in a packed column or by modifications in the synthesis process, e.g. by incremental addition of catalyst, by increasing the final reaction temperature, by programmed addition of monomers, by addition of initiator at the final stage of reaction, by longer reaction time or any combination of these procedures or any other convenient technique.

EXAMPLE 19

Preparation of Vinyl Pyrrolidone/N-[3-(Dimethylamino)Propyl]methacrylamide 100% Quaternized with Diethyl Sulfate To a 1 liter four necked round bottom flask equipped with a mechanical stirrer, a dropping funnel, a condenser and a thermometer, 500 g. deionized water and 75 g. of VP were charged and heated to 61° C. The solution was purged with nitrogen gas for one half hour after which 39.4 g. of DMAPMAA and 60 g. deionized water were added and mixed in the following manner. Specifically, 40 drops of the mixed solution and 10 drops (0.2 g.) of t-butyl peroxypivalate were added to the reaction flask, the solution heated to 66° C. and then the remaining DMAPMAA solution was charged over a period of 2.5 hours. After completing the addition, 5 drops (0.1 g.) t-butylperoxypivalate and 40 g. deionized water were added. After stirring the mixture for 3 hours at 66° C., the reaction flask was cooled to 43° C. and 35.6 g of diethyl sulfate was added over a period of about 25 minutes and stirring was continued at 43° C. for 3 additional hours after which the mixture was cooled to room temperature.

The quaternized product in about 99% yield was recovered as a liquid.

The quaternized product containing 50% VP in 20% in solution, was found to have a residual VP of 0.17 wt. %; residual DMAPMAA of 0.70 wt. %; a Brookfield viscosity (#4 spindle, 30 rpm at 25° C.) of 3600 cps; a pH of 3.4 and APHA color determined by D 25-2 Hunterlab Colorimeter of 120.

EXAMPLE 20

As illustrated in Examples 9-18, the polyvinyl pyrrolidone can be polymerized with a prequaternized salt of the tertiary amino acrylamide. The preparation of a quaternized N-[3-(dimethylamino)propyl]methacrylamide monomer was effected as follows.

To a 1 liter four necked round bottom flask equipped with a condenser, a mechanical stirrer, a thermometer and a dropping funnel, 50 g. (0.294 mol) of DMAP-MAA and 530 g. of toluene were charged. 1,2-oxathiolane-2,2-di-one (PS), 38.4 g. (0.294 mole) was melted at about 40° C. and added dropwise over a period of 20 minutes. The mixed solution was heated to reflux for one half hour and then cooled to room temperature. The solution was stirred for another 4.5 hours and the precipitated product was collected after filtration, washed with acetone and dried in a vacuum oven at 50° C. The product,

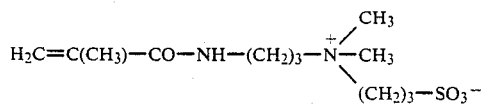

which is the inner salt of 3-[dimethyl-(3-methacrylamido propyl)amino]propanesulfonic acid, was identified by IR, H-1 NMR and C-13 NMR and was recovered in quantitative yield.

EXAMPLE 21

Another quaternized salt monomer of N-[3-(dimethylamino)propyl]methacrylamide was prepared as follows.

To a 1 liter four necked round bottom flask equipped with a thermometer, a condenser, a dropping funnel, and a mechanical stirrer, 33.62 g. (0.198 mol) of DMAP-MAA and 500 ml of toluene were charged and mixed after which 26.4 g. (0.198 mol) of chloromethyl pyrrolidone (CMP), was added dropwise from dropping funnel over a period of 20 minutes. The exothermic reaction raised the temperature from 25° C. to 38° C. The product as a white precipitate came out of the solution in 10 minutes. The solution was stirred for another 5 hours at room temperature and the product was isolated after filtration and dried in the vacuum oven at 50° C. The product

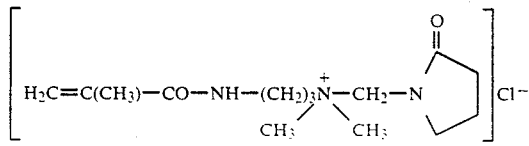

which is (3-methacrylamidopropyl)dimethyl[(2-oxopyrrolidin-1-yl)-methyl]ammonium chloride, was identified by IR and H-1 NMR and was recovered in quantitative yield.

It is to be understood that any of the aforementioned acrylamides or methacrylamides can be substituted in examples 1-19 and 21-22 to provide the corresponding copolymeric products and that any of the aforementioned salt comonomers can be substituted in example 20 to provide the corresponding quaternized products of this invention.

EXAMPLE 22

Example 1 was repeated except that 1,2-oxathiolane-2,2-di-one,

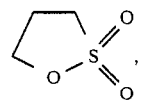

was substituted for diethyl sulfate. The copolymer defined by the formula

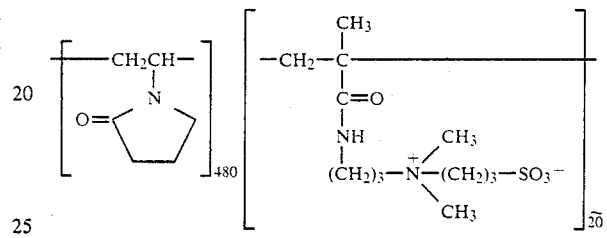

which is the inner salt of 3-[dimethyl-(3-methacrylamido propyl)amino]propanesulfonic acid, was identified by IR, H-1 NMR and C-13 NMR and was recovered in quantitative yield.

EXAMPLE 23

Example 1 was repeated except that N-chloromethyl pyrrolidone was substituted for diethyl sulfate and dimethyl sulfoxide is substituted for water as the solvent. The product having the formula

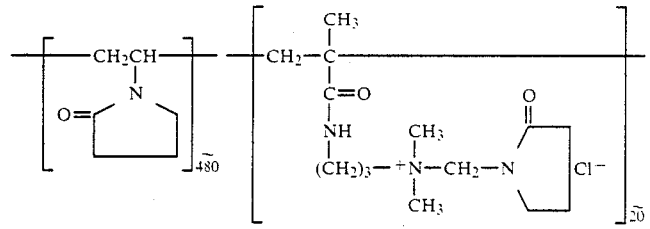

which is (3-methacrylamido propyl)dimethyl [(2-oxopyrrolidin-1-yl)methyl]ammonium chloride, was identified by IR and H-1 NMR and was recovered in quantitative yield.

EXAMPLE 24

N-vinyl pyrrolidone/dimethylaminoethyl methacrylate copolymers, as a 20% active aqueous solution and having a pH of 5-7, are stable in neutral or acid based formulations; however their stability diminishes at higher pH. Accordingly, there is a need for a cationic polymer for use in alkaline formulations such as hair perms, hair dyes, antiperspirants, skin creams, antiseptics, cleansing solutions which retain the excellent properties of the above copolymers in cosmetic, cleaners, antibiotic and hair treating formulations. The present polymers satisfy this need and provide high stability at pH of 10 or more as shown in following Table IV where polymers of the above examples are compared with the N-vinylpyrrolidone/dimethylamino methacrylate copolymer, a yellow liquid (80 VP/20 DMAEMA) 50% quaternized with diethylsulfate having a Brookfield viscosity at 25° C. of about 45,000 cps.

The polymers for this test are prepared by adjusting the pH of the polymer solution to 7 or 10 by adding dropwise a 50% active sodium hydroxide solution until the desired pH of 10 is obtained or similarly by adding dropwise a 50% active solution of concentrated sulfuric acid until a pH of 7 is obtained.

TABLE IV

| Polymer of Example | Temperature °C./pH | % Hydrolysis Months | | | |
|---|---|---|---|---|---|
| | | 1 | 2 | 3 | 4 |
| 16 | 45/10 | 5 | 12 | — | 22 |
| 16 | 25/10 | 5 | 12 | — | 8.8 |
| 16 | 45/7 | 5 | 8 | — | 18.8 |
| 16 | 25/7 | 5 | 8 | — | 10.8 |
| 6 | 45/10 | 5 | 3 | — | 10 |
| 6 | 25/10 | 5 | 3 | — | 4 |
| 6 | 45/7 | 5 | 10 | — | 16 |
| 6 | 25/7 | 5 | 10 | — | 8 |
| 24 | 45/10 | 30 | | 51.0 | 90 |
| 24 | 25/10 | 14 | | 14.4 | 30.6 |
| 24 | 45/7 | 8.5 | | 15.6 | 22.9 |
| 24 | 25/7 | 0 | | 0 | 4.8 |

As is indicated in the above Table, the present polymers are significantly more stable under conditions of elevated temperature and pH greater than 7. It was found that the amido linkage in the present polymers has much more resistance to hydrolysis than the ester linkage of the quaternized polymer of Example 24.

EXAMPLE 25

The compatibility of the present polymers with commonly used surfactants was also tested by forming aqueous solutions of 1% and 3% polymer solids with respectively 15% and 13.4% active surfactant and mixing for a period of 30-60 minutes at room temperature. The results of these tests are reported in following Table V.

TABLE V

| Polymer of Example | Ammonium Lauryl Sulfate | | Sodium Lauryl Sulfate | | Sodium Laureth-Sulfate | | Triethanol amine Lauryl Sulfate | |
|---|---|---|---|---|---|---|---|---|
| | % Polymer Solids/% Surfactant | | | | | | | |
| | 1/15 | 3/13.4 | 1/15 | 3/13.4 | 1/15 | 3/13.4 | 1/15 | 3/13.4 |
| 1 | C | C | C | C | C | C | C | C |
| 2 | C | C | C | C | C | C | C | C |
| 3 | I | I | I | I | I | I | I | I |
| 4 | C | C | C | C | C | C | C | C |
| 5 | C | C | C | C | C* | C | C | C |
| 6 | I | I | I | I | I | I | I | I |
| 8 | C | C | C | C | C | C | C | C |
| 10 | C | C | C | C | C | C | C | C |
| 12 | C | C | C | C | C | C | C | C |
| 14 | C | C | C | C | C | C | C | C |
| 15 | C | I | C | C | C | C | C | C |
| 16 | I | I | C | C | I | C | I | I |

TABLE V-continued

| Polymer of Example | Ammonium Lauryl Sulfate | | Sodium Lauryl Sulfate | | Sodium Laureth-Sulfate | | Triethanol amine Lauryl Sulfate | |
|---|---|---|---|---|---|---|---|---|
| 17 | C | C | C | C | C | C* | C | C |
| 18 | I | I | I | I | I | I | I | I |

*clear with very slight haze
C signifies compatible
I signifies incompatible

EXAMPLE 26

The filming properties of the present polymers were also tested by forming ethanol solutions containing 2% polymer solids. These solutions were tested at 25.8° C. and 35.2% relative humidity. The films were prepared by drawing a 0.006 inch thick wet film using the film applicator on the glass plate and allowing it to dry thoroughly. The films were evaluated on the basis of:

a. Appearance of the film—visual observation for clarity and gloss.
b. Flexibility—Response to scraping the film with the knife point. Formation of a continuous thin curl of film denotes flexibility whereas chipping denotes brittleness.
c. Ability to withstand scoring of the film with pencils from a set of hardness testing pencils*. The highest degree of pencil hardness that does not scratch the film surface is recorded in Table VI.
* Pencil hardness from soft to hard: 6B, 5B, 4B, 3B, 2B, B, HB, F, H, 2H, 3H, 4H, 5H, 6H, 7H, 8H and 9H.

d. Dry Tackiness—Noted by touching dry fingertips on the film surface for about a second after which the evidence of tack is noted.
e. Moist tackiness—Fingertips are slightly moistened by exhaling onto the palm to create dampness. The finger tips are pressed onto the palm for about ten seconds, removed, and immediately placed on the film surface for about one second and then removed. The evidence of tackiness is noted.
f. Water Spotting—Three drops of water are placed about 0.5 inch apart on the film. The appearance of the film through the water spot is noted as clear, hazy, or cloudy. These observations are made over a five minute period. If the film is disturbed within the first 15 seconds, this indicates that the film is water sensitive.
g. Redispersion—One of the drops of water is stirred after five minutes. The ease of redispersability is noted.
h. Appearance after drying—After the water drops have been completely evaporated the film is examined for clarity, smoothness and gloss.

The data compiled in these tests represents a means of predicting the utility of the polymeric resin in hair toiletry formulations.

The results of these tests is summarized in following Table VI.

TABLE VI

| Polymer of Example No. | Appearance | Flexibility | Tack | | Water Spotting | | Redispersion | Appearance after drying | Pencil Hardness |
|---|---|---|---|---|---|---|---|---|---|
| | | | Dry | Moist | Initial | 5 min. | | | |
| 1 | C,G | F | none | v.s. | C | C | good | C | HB |
| 2 | C,G | F | none | v.s. | C | C | good | C | H |
| 3 | C,G | F | none | moderate | C | C | good | C | HB |
| 4 | C,G | F | none | v.s. | C | C | good | C | 3H |
| 5 | C,G | F | none | v.s. | C | C | good | C | F |
| 6 | C,G | F | none | v.s. | C | C | good | C | H |

TABLE VI-continued

| Polymer of Example No. | Appearance | Flexibility | Tack Dry | Tack Moist | Water Spotting Initial | Water Spotting 5 min. | Redispersion | Appearance after drying | Pencil Hardness |
|---|---|---|---|---|---|---|---|---|---|
| 8 | C,G | F | none | s. | C | C | good | C | 2H |
| 10 | C,G | F | none | v.s. | C | C | good | C | F |
| 14 | C,G | F | none | v.s. | C | C | good | C | H |
| 15 | C,G | F | none | v.s. | C | C | good | cloudy center spots | F |
| 16 | C,G | F | none | s. | C | C | good | C | 3H |
| 17 | C,G | F | none | v.s. | C | C | good | center of one drop cloudy | H |
| 18 | hazy,G | F | none | v.s. | slight haze | slight haze | good | C | H |

C = clear;
G = glossy;
F = flexible;
s = slight;
v.s. = very slight

EXAMPLE 27

The following tests on wet combability were conducted under ambient conditions. A hair sample was immersed in a glass beaker filled with distilled water for 10 seconds after which the sample was removed and squeezed to remove excess water. The sample was then combed 3 times to evaluate wet comb drag and the result recorded in Table VII.

The damp sample was then immersed in a 1% aqueous solution of the present polymer for one minute, squeezed to remove excess water and combed 3 times to determine wet comb drag. This result was also recorded in Table VII.

Finally the polymer coated sample was rinsed in a glass beaker of distilled water for 30 seconds while dipping up and down 10 times and then transferred to another beaker of distilled water where it was rinsed for 30 seconds by dipping up and down 10 times. The sample was then squeezed to remove excess water and wet comb drag determined and recorded as in Table VII.

TABLE VII

| Polymer of Example No. | WET COMBABILITY AFTER DIPPING IN WATER | WET COMBABILITY AFTER DIPPING IN POLYMER | WET COMPATIBILITY AFTER RINSING |
|---|---|---|---|
| 1 | 2 | 7 | 6 |
| 2 | 2 | 6 | 4 |
| 3 | 1 | 4 | 6 |
| 4 | 1 | 5 | 6 |
| 5 | 2 | 5 | 5 |
| 6 | 2 | 7 | 5 |
| 8 | 2 | 5 | 4 |
| 10 | 2 | 7 | 4 |
| 12 | 1 | 6 | 4 |
| 14 | 1 | 4 | 7 |
| 15 | 1 | 5 | 6 |
| 16 | 2 | 4 | 3 |
| 17 | 2 | 5 | 4 |
| 18 | 1 | 5 | 4 |
| 24 | 2 | 7 | 6 |

Evaluations in the above Table range from 1 to 10 with the following designations:
10 No drag (comb falls through).
9 Very, very slight drag.
8 Very slight drag.
7 Slight drag.
6 Slight to moderate drag.
5 Moderate drag.
4 Moderate to considerable drag.
3 Considerable drag.
2 Heavy drag.
1 Very heavy drag (can't get comb through).

EXAMPLE 28

Tests were made on several of the present polymers to determine their properties in hair treatment formulations. Aqueous solutions of the polymers were made and tested on untreated human hair under the conditions reported in Table VIII. Each hair sample was ten inches long and weighed 3 grams and 3 samples were used for each product tested. About 1.5 ml of polymer solution was poured and rubbed into the hair shaft, combed twice and then curled on a 1 inch smooth plastic hair roller. The samples were then dried for 1 hour on the hot setting of a commercial hair dryer after which the hair samples were carefully uncurled and evaluated on the basis of the following scoring values. The results of these tests are reported in Table VIII.

HAIR CHARACTERISTICS - SCORING VALUES

A. STIFFNESS
1 Very, very soft (like natural hair)
2 Very soft
3 Soft
4 Moderately soft
5 Slightly soft
6 Moderately stiff
7 Stiff to moderately stiff
8 Stiff
9 Very stiff
10 Very, very stiff (like a board)

B. CURL SNAP
1 No springback (completely falls out)
2 Very poor springback
3 Poor springback
4 Fair to poor springback
5 Fair springback
6 Moderate springback
7 Moderate to good springback
8 Good springback
9 Very good springback
10 Excellent springback (return like an elastic band)

C. COMB DRAG
1 Very heavy drag (can't get comb through)
2 Heavy drag
3 Considerable drag
4 Moderate to considerable drag
5 Moderate drag
6 Slight to moderate drag
7 Slight drag
8 Very slight drag
9 Very, very slight drag
10 No drag (comb falls through)

D. COMB RESIDUE
1 Very heavy - completely coated comb
2 Heavy
3 Considerable - flaking on both sides of comb
4 Considerable
5 Visible - flakes
6 Visible - powdery
7 Slightly visible
8 Very slightly visible
9 Very, very slightly visible
10 None E. HAIR RESIDUE
1 Extremely heavy (hair is totally coated)
2 Heavy
6 Visible - powdery
7 Slightly visible
8 Very slightly visible

-continued
HAIR CHARACTERISTICS - SCORING VALUES

3 Considerable to heavy
4 Considerable
5 Visible - flakes

9 Very, very slightly visible
10 None

F. MANAGEABILITY

1 Straight
2 Almost straight
3 Open curl
4 Partially opened curl
5 Slight bounce 6 Slight to moderate bounce
7 Moderate bounce
8 Bouncy and springy curl
9 Tight full bouncy and springy curl
10 Very tight (short full curl

G. STATIC

1 Total fly away (impossible to manage after first brushing)
2 Excessive fly away
3 Considerable fly away
4 Moderate to considerable fly away
5 Moderate fly away 6 Slight to moderate fly away
7 Slight
8 Very slight
9 Very, very slight
10 None (no free hair movement)

TABLE VIII

|  | Stiffness | Curl Snap | Comb Drag | Residue on Comb | Residue on Hair | Manageability | Static |
|---|---|---|---|---|---|---|---|
| 1% Solids, 79° F., 81% rel. Humidity |  |  |  |  |  |  |  |
| Polymer of Example No. 5 | 3.0 | 5.0 | 8.7 | 7.0 | 10.0 | 5.3 | 4.0 |
| Polymer of Example No. 24 | 3.3 | 5.0 | 9.3 | 8.7 | 10.0 | 5.3 | 4.0 |
| 1% Solids, 79° F., 75% rel. Humidity |  |  |  |  |  |  |  |
| Polymer of Example No. 3 | 2.3 | 7.0 | 7.7 | 9.0 | 9.7 | 4.0 | 4.7 |
| Polymer of Example No. 6 | 3.0 | 7.0 | 8.0 | 9.3 | 9.7 | 4.7 | 4.0 |
| Polymer of Example No. 16 | 2.7 | 6.0 | 8.0 | 8.7 | 9.7 | 4.7 | 4.3 |
| Polymer of Example No. 24 | 2.3 | 5.7 | 8.3 | 9.0 | 9.7 | 4.0 | 5.3 |
| 1% Solids, 82° F., 61.5% rel. Humidity |  |  |  |  |  |  |  |
| Polymer of Example No. 4 | 4.0 | 6.0 | 7.7 | 8.7 | 9.7 | 7.0 | 2.7 |
| Polymer of Example No. 14 | 6.0 | 7.7 | 9.0 | 9.7 | 9.7 | 7.0 | 3.3 |
| Polymer of Example No. 15 | 3.7 | 4.3 | 8.3 | 9.0 | 9.3 | 4.0 | 3.3 |
| Polymer of Example No. 24 | 3.3 | 5.7 | 6.7 | 9.3 | 9.7 | 4.3 | 3.0 |
| 1% Solids, 79° F., 70% rel. Humidity |  |  |  |  |  |  |  |
| Polymer of Example No. 2 | 3.0 | 6.3 | 6.7 | 9.3 | 9.7 | 4.3 | 1.7 |
| Polymer of Example No. 12 | 3.0 | 6.0 | 9.0 | 9.3 | 9.3 | 4.0 | 2.0 |
| Polymer of Example No. 18 | 2.7 | 6.0 | 8.3 | 9.3 | 9.7 | 4.7 | 2.0 |
| Polymer of Example No. 24 | 4.3 | 7.3 | 8.0 | 9.3 | 9.7 | 4.0 | 2.0 |
| 1% Solids, 74° F., 68% rel. Humidity |  |  |  |  |  |  |  |
| Polymer of Example No. 1 | 4.0 | 6.3 | 8.0 | 9.0 | 9.7 | 5.0 | 2.3 |
| Polymer of Example No. 8 | 4.0 | 5.3 | 9.0 | 9.0 | 9.7 | 4.7 | 2.0 |
| Polymer of Example No. 10 | 3.0 | 5.3 | 9.0 | 9.3 | 9.7 | 5.0 | 1.3 |
| Polymer of Example No. 24 | 4.0 | 5.3 | 8.3 | 9.3 | 9.7 | 4.3 | 1.3 |
| 1% Solids, 78° F., 68.5% rel. Humidity |  |  |  |  |  |  |  |
| Polymer of Example No. 17 | 5.7 | 7.3 | 7.3 | 9.7 | 9.3 | 5.5 | 2.7 |
| Polymer of Example No. 24 | 4.8 | 6.3 | 9.0 | 9.7 | 9.7 | 5.3 | 2.3 |

Other quaternized lactam/amino amide copolymers of this invention provide hair and skin benefits comparable with quaternized VP/DMAPMAA shown above.

EXAMPLE 29

Preparation of Vinyl Pyrrolidone/N-[4-(Diethylamino)butyl]acrylamide 100% quaternized with 1,2-oxathiolane-2,2-dione To a 1 liter four necked round bottom flask equipped with a mechanical stirrer, a dropping funnel, a condenser and a thermometer, 500 g. deionized water and 75 g. of VP are charged and heated to 61° C. The solution is purged with nitrogen gas for one half hour after which 45 g. of the inner salt of 3-[diethyl-(4-acrylamido butyl) amino]propanesulfonic acid and 60 g. of deionized water are added and mixed in the following manner. Specifically, 40 drops of the mixed solution and 10 drops (0.2 g.) of t-butyl peroxypivalate are added to the reaction flask, the solution heated to 66° C. and then the remaining portion of said inner salt solution is charged over a period of 2.5 hours. After completing the addition, 5 drops (0.1 g.) t-butylperoxypivalate and 40 g. deionized water are added. The mixture stirred for 3 hours at 66° C. cooled to room temperature and 100% quaternized product having the random structure,

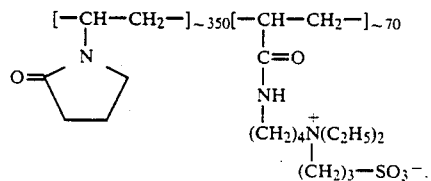

is recovered.

EXAMPLE 30

Preparation of Vinyl Pyrrolidone/N-[14-(Dimethylamino)tetradecyl]acrylamide 100% Quaternized with N-chloromethyl pyrrolidone To a 1 liter four necked round bottom flask equipped with a mechanical stirrer, a dropping funnel, a condenser and a thermometer, 500 g. deionized water and 75 g. of VP are charged and heated to 61° C. The solution is purged with nitrogen gas for one half hour after which 30 g. of (14-acrylamido tetradecyl)dimethyl[(2-oxopyrrolidin-1-yl)-methyl]ammonium chloride and 60 g. of deionized water are added and mixed in the following manner. Specifically, 40 drops of the mixed solution and 10 drops (0.2 g.) of t-butyl peroxypivalate are added to the reaction flask, the solution is heated to 66° C. and then the remaining N-[14-(dimethylamino)-tetradecyl]acrylamide solution is charged over a period of 2.5 hours. After completing the addition, 5 drops (0.1 g.) t-butylperoxypivalate and 40 g. deionized water are added. The mixture stirred for 3 hours at 66° C., cooled to room temperature and recovered in 95% yield as a quaternized product having the random structure

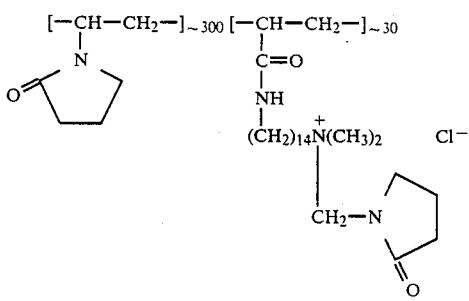

It is to be understood that the above examples are provided to illustrate specific and preferred embodiments of the invention and that many modifications and alterations can be made in these examples without departing from the scope of the invention. For example it will be found that the pyrrolidonyl salt compounds are excellent hair dye leveling agents and are soluble in most dye formulations. The sultone salts, because of the negative and positive charges in the polymer, are superior surfactants in conditioning shampoos. Also other lactam copolymers of this invention, e.g. N-vinylcaprolactam and N-vinyl-3-methyl pyrrolidone, etc. provide the above described benefits.

What is claimed is:

1. A stable, non-irritating hair care composition having conditioner action comprising an aqueous solution of pH about 10 characterized by containing about 0.05 to about 8% by weight of a copolymer of about 50 to 99 mole % vinyl pyrrolidone and 1 to about 50 mole % of a quaternized amino acrylamide which is (3-methacrylamidopropyl) trimethylammonium chloride "having less than 7 wt. % residual monomer content".

2. A stable, non-irritating hair care composition according to claim 1 having about 0.17 wt. % or less residual vinyl pyrrolidone monomer and about 0.70 wt. % or less residual (3-methacrylamidopropyl) trimethylammonium chloride monomer.

3. A stable, non-irritating hair care composition according to claim 1 wherein said residual monomer content is less than 2 wt. %.

* * * * *